US011202807B2

(12) United States Patent
De Vos et al.

(10) Patent No.: US 11,202,807 B2
(45) Date of Patent: Dec. 21, 2021

(54) BACTERIAL SPECIES

(71) Applicant: WAGENINGEN UNIVERSITEIT, Wageningen (NL)

(72) Inventors: Willem Meindert De Vos, Ede (NL); Clara Belzer, Wageningen (NL)

(73) Assignee: WAGENINGEN UNIVERSITEIT, Wageningen (NL)

( * ) Notice: Subject to any disclaimer, the term of this patent is extended or adjusted under 35 U.S.C. 154(b) by 121 days.

(21) Appl. No.: 16/093,041

(22) PCT Filed: Apr. 11, 2017

(86) PCT No.: PCT/EP2017/058700
§ 371 (c)(1),
(2) Date: Oct. 11, 2018

(87) PCT Pub. No.: WO2017/178496
PCT Pub. Date: Oct. 19, 2017

(65) Prior Publication Data
US 2019/0183941 A1   Jun. 20, 2019

(30) Foreign Application Priority Data

Apr. 11, 2016 (EP) .................................... 16164743

(51) Int. Cl.
*A61K 35/741* (2015.01)
*C12N 1/20* (2006.01)
*A61K 35/00* (2006.01)
*C12R 1/01* (2006.01)

(52) U.S. Cl.
CPC .............. *A61K 35/741* (2013.01); *C12N 1/20* (2013.01); *C12N 1/205* (2021.05); *A61K 2035/115* (2013.01); *C12R 2001/01* (2021.05)

(58) Field of Classification Search
CPC .. A61K 35/741; A61K 2035/115; C12N 1/20; C12R 1/01
See application file for complete search history.

(56) References Cited

U.S. PATENT DOCUMENTS

| 9,433,650 | B2 | 9/2016 | Nieuwdorp et al. |
| 9,623,055 | B2 | 4/2017 | Nieuwdorp et al. |
| 9,669,059 | B2 | 6/2017 | Wang |
| 2014/0242654 | A1 | 8/2014 | Levinson |
| 2015/0306152 | A1 | 10/2015 | Cani et al. |

FOREIGN PATENT DOCUMENTS

| WO | 2013/032328 A1 | 3/2013 |
| WO | 2014/075745 A1 | 5/2014 |
| WO | 2014/076246 A1 | 5/2014 |
| WO | 2014/150094 A1 | 9/2014 |

OTHER PUBLICATIONS

Anhê et al., Gut, 2015, vol. 64, p. 872-883, Published Online on Jul. 30, 2014.*
Rajilić-Stojanović et al., "The first 1000 cultured species of the human gastrointestinal microbiota", FEMS Microbiology Reviews, 2014, pp. 996-1047, vol. 38, Issue 5.
Everard et al., "Responses of Gut Microbiota and Glucose and Lipid Metabolism to Prebiotics in Genetic Obese and Diet-Induced Leptin-Resistant Mice", Diabetes, 2011, pp. 2775-2786, vol. 60, No. 11.
Reunanen et al., "Akkermansia muciniphila Adheres to Enterocytes and Strengthens the Integrity of the Epithelial Cell Layer", Applied and Environmental Microbiology, 2015, pp. 3655-3662, vol. 81, No. 11.
Bischoff et al., Intestinal permeability—a new target for disease prevention and therapy, BMC Gastroenterology, 2014, vol. 14, No. 189.
Ouwerkerk et al., "*Akkermansia glycaniphila* sp. nov., an anaerobic mucin-degrading bacterium isolated from reticulated python faeces", International Journal of Systematic and Evolutionary Microbiology, 2016, pp. 4614-4620, vol. 66.
Smith et al., The Microbial Metabolites, Short-Chain Fatty Acids, Regulate Colonic Treg Cell Homeostasis, 2013, pp. 569-573, vol. 341, No. 6145.
Erny et al, Host microbiota constantly control maturation and function of microglia in the CNS, Nature Neuroscience, 2015, pp. 965-977, vol. 18, No. 7.
Hosseini et al., "Propionate as a health-promoting microbial metabolite in the human gut", Nutrition Reviews, 2011, pp. 245-258, vol. 69, No. 5.
Chambers et al., "Effects of targeted delivery of propionate to the human colon on appetite regulation, body weight maintenance and adiposity in overweight adults", Gut, 2015, pp. 1744-1754, vol. 64, No. 11.
Belzer et al., "Winogradsky Review: Microbes inside—from diversity to function: the case of Akkermansia", The ISME Journal, 2012, pp. 1449-1458, vol. 6.
Solanki et al., "Development of Microencapsulation Delivery System for Long-Term Preservation of Probiotics as Biotherapeutics Agent", BioMed Research International, 2013, Article ID: 620719.
Anhê et al., "Triggering Akkermansia with dietary polyphenols: A new weapon to combat the metabolic syndrome?", Gut Microbes, 2016, pp. 146-153, vol. 7, No. 2.
Derrien et al., "*Akkermansia muciniphila* gen. nov., sp. nov., a human intestinal mucin-degrading bacterium", International Journal of Systematic and Evolutionary Microbiology, 2004, pp. 1469-1476, vol. 54.
Suzuki et al., "Quantitative Analysis of Small-Subunit rRNA Genes in Mixed Microbial Populations via 59-Nuclease Assays", Applied and Environmental Microbiology, 2000, pp. 4605-4614, vol. 66, No. 11.

(Continued)

*Primary Examiner* — Kade Ariani
(74) *Attorney, Agent, or Firm* — Nixon & Vanderhye

(57) ABSTRACT

A novel *Akkermansia* species has been isolated from fresh faeces obtained from the reticulated python. The species has been named *Akkermansia glycaniphilus*. It is capable of growing on mucus as a sole carbon and nitrogen source. The species can be used as a medicament, probiotic or cosmetic, e.g., for promoting weight loss, for promoting gut mucosal immune system function, for maintaining, restoring and/or increasing the physical integrity of the gut mucosal barrier, and for prevention or treatment of a variety of associated diseases or disorders.

7 Claims, No Drawings

(56) References Cited

OTHER PUBLICATIONS

Pruesse et al., "SINA: Accurate high-throughput multiple sequence alignment of ribosomal RNA genes", Bioinformatics, 2012, pp. 1823-1829, vol. 28, No. 14.
Ludwig et al., "ARB: a software environment for sequence data", Nucleic Acids Research, 2004, pp. 1363-1371, vol. 32, No. 4.
Boisvert et al., "Ray Meta: scalable de novo metagenome assembly and profiling", Genome Biology, 2012, vol. 13, Article ID: R122.
Hyatt et al., "Prodigal: prokaryotic gene recognition and translation initiation site identification", BMC Bioinformatics, 2010, vol. 11, Article ID:119.
Hunter et al.,"InterPro in 2011: new developments in the family and domain prediction database", Nucleic Acids Research, 2012, pp. D306-D312, vol. 40.
Lowe et al., "tRNAscan-SE: a program for improved detection of transfer RNA genes in genomic sequence", Nucleic Acids Research, 1997, pp. 955-964, vol. 25, No. 5.
Lagesen et al.,"RNAmmer: consistent and rapid annotation of ribosomal RNA genes", Nucleic Acids Research, 2007, pp. 3100-3108, vol. 35, No. 9.
Suzek et al., "UniRef: comprehensive and non-redundant UniProt reference clusters", Bioinformatics, 2007, pp. 1282-1288, vol. 23, No. 10.
Claudel-Renard et al., "Enzyme-specific profiles for genome annotation: PRIAM", Nucleic Acids Research, 2003, pp. 6633-6639, vol. 31, No. 22.
Burge et al., "Rfam 11.0: 10 years of RNA families", Nucleic Acids Research, 2013, pp. D226-D232, vol. 41, Database issue.
De Ley et al., "The quantitative measurement of DNA hybridization from renaturation rates", European Journal of Biochemistry, 1970, pp. 133-142, vol. 12.
Mesbah et al., "Precise Measurement of the G+C Content of Deoxyribonucleic Acid by High-Performance Liquid Chromatography", International Journal of Systematic Bacteriology, 1989, pp. 159-167, vol. 39, No. 2.
Tindall et al., "Notes on the characterization of prokaryote strains for taxonomic purposes", International Journal of Systematic and Evolutionary Microbiology, 2010, pp. 249-266, vol. 60.
Goris et al., "DNA-DNA hybridization values and their relationship to whole-genome sequence similarities", International Journal of Systematic and Evolutionary Microbiology, 2007, pp. 81-91, vol. 57.
Van Passel et al., "The Genome of Akkermansia muciniphila, a Dedicated Intestinal Mucin Degrader, and Its Use in Exploring Intestinal Metagenomes", Plos One, 2011, Article ID: e16876, vol. 6, No. 3.
Linden et al., "Mucins in the mucosal barrier to infection", Mucosal Immunology, 2008, pp. 183-197, vol. 1, No. 3.
Costello et al., "Postprandial remodeling of the gut microbiota in Burmese pythons", The ISME Journal, 2010, pp. 1375-1385, vol. 4.
International Search Report and Written Opinion, dated May 16, 2017, from corresponding PCT application No. PCT/EP2017/058700.
Chinese Search Report for Chinese Patent Application No. 2017800318088 dated Jul. 15, 2021, 6 pages.
Peng et al., "Recent Advances of Diagnosis and Therapeutics of Clinical Endocrine Diseases," Xian Jiaotong University Press, Chapter 16, metabolic syndrome, pp. 416-418, published on Nov. 30, 2014.

\* cited by examiner

BACTERIAL SPECIES

FIELD OF THE INVENTION

The present invention relates to the prevention and/or treatment of metabolic disorders, such as metabolic disorders related to overweight and obesity, e.g., type 2 diabetes mellitus and high cholesterol. The invention also relates to a method of modulating and/or promoting gut mucosal immune system function and/or maintaining and/or restoring and/or increasing the physical integrity of the gut mucosal barrier in a mammal, e.g., a human or a pet or a production animal.

BACKGROUND OF THE INVENTION

Obesity is primarily a consequence of detrimental nutritional and physical habits against an unfavourable genetic background. It has serious health consequences, including increased risk for type 2 diabetes mellitus, cardiovascular disease, pulmonary hypertension, sleep apnoea, and a number of cancers, and is strongly linked to an increased risk of mortality.

The human intestinal tract contains a large variety of micro-organisms, of which bacteria are the most dominant and diverse. As a whole, the microbiome is more than 100 times larger than the human genome. Thus, intestinal microbiota can be viewed as an 'exteriorised organ' that contributes to overall metabolism and plays a role in converting food into nutrients and energy. The community of at least $10^{14}$ bacteria is dominated by anaerobic bacteria and composed of several thousands of species, from which now 1000 have been cultured (Rajilic Stojanovic and de Vos, 2014, FEMS Microbiol Rev 38: 996-1047).

There is growing evidence for the role of intestinal microbiota in host metabolism. It is currently thought that the homeostasis of the gut bacteria depends on host characteristics (age, gender, genetic background, and so on), environmental conditions (stress, drugs, gastrointestinal surgery, and so on), as well as diet.

When treated with prebiotic, diet-induced obese and diabetic mice displayed improved glucose and lipid metabolisms, reduced plasma LPS and improved gut barrier function (e.g., reduction of inflammation), an increased enteroendocrine L-cell number, and improved leptin sensitivity and glucose homeostasy (Everard et al., Diabetes, 2011, vol. 60(11):2775-86). Prebiotic treatment considerably altered the gut microbiota composition in these mice, with, among others, a strongly increased abundance of *Akkermansia muciniphila*.

It was found that oral administration of *A. muciniphila* to mice fed a control diet or a high-fat (HF) diet normalized diet-induced metabolic endotoxemia, adiposity and adipose tissue CD11c marker without any changes in food intake (WO2014/075745). Moreover, *A. muciniphila* treatment reduced body weight and improved body composition (i.e., fat/lean mass ratio). It was found that under HF-diet, *A. muciniphila* treatment increased mRNA expression of markers of adipocyte differentiation and lipid oxidation without affecting lipogenesis. It was also found that colonization with *A. muciniphila* completely reversed diet-induced fasting hyperglycemia, and the insulin-resistance index was similarly reduced after treatment. Finally, it has been found that *A. muciniphila* increases the intestinal barrier function (J Reunanen et al. 2015, Appl Environ Microbiol. 81:3655-62.). It is this intestinal barrier that protects us from pathogens and harmful intestinal components, while a compromised barrier function is associated with various diseases and disorders, including IBS, IBD and others related to gut health. Recently, the intestinal barrier has been defined as a functional entity separating the gut lumen from the inner host, and consisting of mechanical, humoral, immunological, muscular and neurological elements (S C Bishoff et al, 2014, BMC Gastroenterol. 14:189). Hence, improving the intestinal permeability that can be defined as a measurable feature of the intestinal barrier, is an important factor contributing that affects gut health.

To be useful in the intestinal tract, a probiotic bacterium should be active at the appropriate location in the intestinal tract. The intestinal tract of human and other animals has a complex architecture where notably the pH differences are enormous. In the human intestinal tract the intraluminal pH is approximately pH 6 in the duodenum following the acid stomach, increases in the small intestine from pH 6 to pH 7.4 in terminal ileum, drops to pH 5.7 in the caecum and gradually increase to reach pH 6.7 in the rectum. In some animals quite variable pHs are encountered and in dogs the pH is usually higher than in human, up to pH 7.3 while in cats these may be lower below pH 6.6, also depending on the breed. Changes may occur depending on the diet, age and disease. The pH reflects the 10 base logarithm of the proton concentrations and hence a change in pH of one unit represents a ten-fold difference in proton concentration. Hence it would be of interest to have probiotics that would act at different pH values both for application in human as well as pets or production animals.

It is an aim of the present invention to provide a novel probiotic that is useful for preventing and/or treating metabolic disorders and/or improving intestinal barrier function.

SUMMARY OF THE INVENTION

The present invention pertains to an isolated *Akkermansia glycaniphilus* strain, which is preferably capable of growing on mucin as sole carbon and nitrogen source, and which is preferably further capable of growing on N-acetylglucosamine, N-acetylgalactosamine, glucose, lactose, maltose or galactose as sole carbon source. In an embodiment, said strain is the strain deposited with the Centraalbureau voor Schimmelcultures as CBS141023, or a strain that has been derived therefrom.

The invention also provides a composition comprising the isolated *Akkermansia glycaniphilus* strain as taught herein and a physiologically acceptable carrier. Said composition may be a pharmaceutical composition, preferably in solid dosage form, such as a capsule, a tablet, or a powder. In an embodiment, said *Akkermansia glycaniphilus* is present in lyophilized or microencapsulated form. Said *Akkermansia glycaniphilus* may be present in an amount ranging from about $10^4$ to about $10^{15}$ cells.

The invention further relates to an isolated *Akkermansia glycaniphilus* strain as taught herein or the composition as taught herein for use as a medicament, for use as a probiotic and/or symbiotic, or for use as a cosmetic. The strain or composition as taught herein may, for example, be used for promoting gut mucosal immune system function, for maintaining, restoring and/or increasing the physical integrity of the gut mucosal barrier in a mammal, for promoting weight loss, and/or for preventing and/or treating a disorder selected from the group consisting of metabolic syndrome, obesity, insulin-deficiency or insulin-resistance related disorders, type 2 diabetes, type 1 diabetes, inflammatory bowel disease (IBD), irritable bowel syndrome (IBS), glucose intolerance, abnormal lipid metabolism, atherosclerosis, hypertension, cardiac pathology, stroke, non-alcoholic fatty liver disease, alcoholic fatty liver disease, hyperglycemia, hepatic steatosis, dyslipidemias, dysfunction of the immune system associated with obesity (weight gain), allergy, asthma, autism, Parkinson's disease, multiple sclerosis, neurodegenerative diseases, depression, other diseases related to compromised barrier function, wound healing, behavioral disorders, alcohol dependence, cardiovascular diseases, high cholesterol, elevated triglycerides, atherosclerosis, sleep apnoea, osteoarthritis, gallbladder disease, cancer, and conditions altering the physical integrity of the gut mucosal barrier such as food allergies, immaturity of the gut, e.g., due to a baby being born prematurely, exposure to radiation, chemotherapy and/or toxins, autoimmune disorders, malnutrition, and sepsis.

In a final aspect, the present invention provides for a method for increasing the level of *Akkermansia glycaniphilus* in the gastrointestinal (GI) tract of a mammal, preferably a human, said method comprising the steps of: administering the isolated *Akkermansia glycaniphilus* strain or the composition as taught herein to said mammal; and promoting the growth of said *Akkermansia glycaniphilus* strain in the GI tract of said mammal by administering a compound selected from the group consisting of compounds comprising glucosamine or derivatives of glucosamine such as N-acetyl-glucosamine as building blocks, and polyphenols, to said mammal.

Definitions

The term 'probiotics' or 'probiotic products' as used herein refers to microorganisms such as intestinal bacteria, which—when administered or ingested in effective amounts—confer health benefits to the host (e.g. humans or mammals). Preferably, probiotics should be alive or viable when administered to a subject so as to allow the probiotics to colonize the large intestine of the host. However, under certain conditions, probiotics may also be dead when administered provided that substances produced by the probiotics still exert probiotic, beneficial effects on the host. Most probiotics or probiotic products are composed of lactic acid bacteria such as Lactobacilli or Bifidobacteria. The skilled person is well-acquainted with the field of probiotics and knows how to select lactic acid bacteria endowed with probiotic activity.

The species with the name "*Akkermansia glycaniphilus*" as referred to herein is the same as the species with the name "*Akkermansia glycaniphila*" as used in, for example, Ouwerkerk et al. (2016. Int J of Syst Evol Microbiol 66:1-7). Therefore, these names can be used interchangeably.

The term 'prebiotics' or 'prebiotic products' as used herein generally refers to compounds that promote the growth and/or activity of GI microorganisms that contribute to the well-being of their host. Prebiotics or prebiotic products consist mainly of fermentable fibers or non-digestible carbohydrates. The fermentation of these fibers by probiotics promotes the production of beneficial end products, such as SCFAs, particularly butyrates. The skilled person is well-acquainted with the field of prebiotics and knows how to select ingredients endowed with prebiotic activity.

The term 'symbiotics' or 'symbiotic products' as used herein generally refers to compositions and/or nutritional supplements combining probiotics and one or more compounds that promote the growth and/or activity of GI microorganisms, such as prebiotics, into one product. The symbiotic beneficially affects the host by improving the survival and colonization of the probiotic in the GI tract, by selectively stimulating the growth and/or by activating the metabolism of the probiotic, thus improving host welfare. The skilled person is well-acquainted with symbiotics and knows how to select ingredients that may be combined into a symbiotic.

The term 'beneficial intestinal bacteria species' as used herein refers to a bacterium species that inhabits (i.e. is innate) the mammalian (e.g. human) intestine and exerts beneficial effect(s) (e.g. protection against pathogenic bacteria species, production of butyric acid and/or butyrate and derivatives, etc.) on the GI, metabolic and other health of a mammal in which it resides. Non-limiting examples of beneficial intestinal bacterial species include lactic acid bacteria from the genera *Lactobacillus* and *Bifidobacterium*. Other non-limiting examples of beneficial intestinal bacterial species include butyrate-producing bacterial species, which use the acetyl-CoA to produce butyric acid and/or butyrate and derivative thereof, such as the bacterial strains disclosed in US2014/0242654, WO 2014/150094 or WO2013032328 A1. Similarly, propionate-producing species can be considered as probiotics as propionate like butyrate controls body weight and insulin sensitivity, signals to the immune system among others via regulatory T cells, and affects neural circuits via the FFAR2 receptor (Canfora et al., 2015. Nature Reviews Endocrinology 11:577-591; Smith et al., 2013. Science 341:569-573: Erny et al., 2015, Nat Neurosci 18:965-977) Propionate is a substrate for hepatic gluconeogenesis and has inhibitory effects on lipid and cholesterol synthesis and protective effects on inflammation and carcinogenesis (Hosseini et al., 2011. Nutrition Reviews 69:245-258). Dietary interventions in human have shown that propionate also has found to increase satiety and regulate appetite, resulting in body weight maintenance in overweight adults (Chambers et al 2015. Gut 64:1744-1754). The term 'pathogenic bacterial species' as used herein refers to a bacterium that inhabits (i.e. is innate) the mammalian (e.g. human) intestine and exerts deleterious effect(s) (e.g. infection) on the GI health of a mammal in which it resides. A notorious non-limiting example of a pathogenic bacterial species is the toxin-producing *Clostridium difficile*.

The term 'effective amount' as used herein refers to an amount necessary to achieve an effect as taught herein. The effective amount can be readily determined without undue experimentation by a person of ordinary skill in the art.

The term 'a strain that derives therefrom' as used herein relates to strains obtained by using the deposited strain as taught herein as starting material. The strain that derives therefrom may be a mutant strain, which may be derived from a strain of the invention by means of, for instance, genetic engineering, radiation, UV light, chemical treatment. Alternatively, such derivative or mutant strain may be a strain derived from the deposited strain as taught herein that has been subjected to growth adaptation to particular conditions resulting in an additional benefit to the derivative strain, such as more rapid growth, better survival in the gut, and so on. It is preferred that the derivative or mutant is functionally equivalent to the deposited strain as taught herein. A preferred derivative or mutant as taught herein has substantially the same activity or function as the deposited strain as taught herein. The derivative or mutant advantageously provides substantially the same benefits to a mammal (e.g. humans or other mammals) administered with said derivative or mutant as would be the case upon administration of the deposited strain. The derivative or mutant strain may also be a spontaneous derivative or mutant strain having the same characteristics as described herein for the deposited strain.

The term 'suitable for consumption' or 'nutritionally acceptable' refers to ingredients or substances, which are generally regarded as safe for human (as well as other mammals) consumption.

The terms 'comprising' or 'to comprise' and their conjugations, as used herein, refer to a situation wherein said terms are used in their non-limiting sense to mean that items following the word are included, but items not specifically mentioned are not excluded. It also encompasses the more limiting verb 'to consist essentially of' and 'to consist of'.

Reference to an element by the indefinite article 'a' or 'an' does not exclude the possibility that more than one of the elements is present, unless the context clearly requires that there be one and only one of the elements. The indefinite article 'a' or 'an' thus usually means 'at least one'.

The terms 'to increase' and 'increased level' and the terms 'to decrease' and 'decreased level' refer to the ability to significantly increase or significantly decrease or to a significantly increased level or significantly decreased level. Generally, a level is increased or decreased when it is at least 5%, such as 10%, 15%, 20%, 25%, 30%, 35%, 40%, 45%, 50% higher or lower, respectively, than the corresponding level in a control or reference. Alternatively, a level in a sample may be increased or decreased when it is statistically significantly increased or decreased compared to a level in a control or reference.

DETAILED DESCRIPTION OF THE INVENTION

Bacteria

The present inventors have isolated a new *Akkermansia* species, strain $Pyt^T$, from the intestine of the reticulated python.

It is a Gram-negative, non-motile, strictly anaerobic, oval-shaped, non-spore-forming bacterium. It is capable of using mucin a sole carbon, energy and nitrogen source, a property which it shares with the human strain *Akkermansia muciniphila* $Muc^T$. Strain $Pyt^T$ could grow on a limited number of single sugars, including N-acetylglucosamine, N-acetylgalactosamine, glucose, lactose, maltose and galactose, but only when a plentiful protein source was provided. Phylogenetic analysis based on 16S rRNA gene sequencing showed strain $Pyt^T$ to belong to the Verrucomicrobiae class I, family Akkermansiaceae, genus *Akkermansia*, with *Akkermansia muciniphila* $Muc^T$ as the closest relative (94.4% sequence similarity). Based on phenotypic, phylogenetic and genetic characteristics, strain $Pyt^T$ represent a novel species within the genus *Akkermansia*, for which the name *Akkermansia glycaniphilus* sp. nov. is proposed, with the type strain $Pyt^T$.

The invention therefore relates to an *Akkermansia glycaniphilus* strain, for example, the type strain PytT, which is the strain deposited at CBS, Centraalbureau voor Schimmelcultures, fungal Biodiversity Centre, Institute of the Royal Netherlands Academy of Arts and Sciences (KNAW), Uppsalalaan 8, 3584 CT Utrecht, The Netherlands, by Wageningen University with the Centraalbureau voor Schimmelcultures, Uppsalalaan 8, the Netherlands, on Feb. 24, 2016, receiving the deposit number CBS141023; or a strain that has been derived therefrom.

In an embodiment, said strain is capable of growing on mucin as sole carbon and nitrogen source. The mucin glycans consist of mainly galactose, N-acetylglucosamine, N-acetylgalactoseamine, and *A. glycaniphilus* strain $Pyt^T$ is able to use these all as growth substrate. In contrast with strain *A. muciniphila* MucT, *A. glycaniphilus* strain $Pyt^T$ is able to use galactose as sole carbon source, while producing mainly propionate, acetate and small amounts of succinate.

While *A. glycaniphilus* strain $Pyt^T$ has a broad pH range in which it can grow optimally, its pH optimum is approximately 0.5 pH units lower than that of *A. muciniphila* $Muc^T$.

It was shown that the gut of obese or overweight subjects was depleted in *Akkermansia muciniphila*, and that *Akkermansia muciniphila* supplementation normalized diet-induced metabolic endotoxemia, adiposity and adipose tissue CD11c marker without any changes in food intake (WO2014/075745). Moreover, *A. muciniphila* treatment reduced body weight and improved body composition (i.e., fat/lean mass ratio). Considering its similarities with *Akkermansia muciniphila*, it is assumed that *Akkermansia glycaniphilus* is capable of preventing and/or treating metabolic disorders in the same fashion as *Akkermansia muciniphila*. Similarly, barrier function that is stimulated by *Akkermansia muciniphila* is expected to be increased by *Akkermansia glycaniphilus* as the latter is found as the only *Akkermansia* spp. on the gut of the python. Similar to *A. muciniphila*, the levels of intestinal *Akkermansia* are increased upon fasting, which is part of the normal life cycle of the python (Belzer and de Vos, 2012, ISME J 6:1449-58)

In an embodiment, said strain is further capable of growing on N-acetylglucosamine, N-acetylgalactosamine, glucose, lactose, maltose or galactose as sole carbon source, and is particularly capable of growing in a basal medium on N-acetylglucosamine, N-acetylgalactosamine, D-glucose, D-lactose or D-galactose in the presence of a suitable nitrogen source, such as tryptone, optionally supplemented with threonine, e.g., in a basal medium on N-acetylglucosamine, N-acetylgalactosamine, D-glucose, D-lactose or D-galactose in the presence of tryptone 16 g $l^{-1}$, and 4 g $l^{-1}$ threonine. Tryptone is a proteolytic digest of casein and can be replaced by other protein sources such as those derived from soy or pea and other plant proteins.

Composition

The present invention also relates to a composition comprising the isolated *Akkermansia glycaniphilus* strain as taught herein and a physiologically acceptable carrier.

In an embodiment, the physiologically acceptable carrier may be any carrier that is suitable for keeping the bacterial strain as taught herein viable until consumption by a subject (e.g. humans and/or animals). For instance, non-limiting examples of acceptable carriers that are suitable for this purpose include any of well-known physiological or pharmaceutical carriers, buffers, and excipients. It will be appreciated that the choice for a suitable physiological or pharmaceutical carrier will depend upon the intended mode of administration of the composition as taught herein (e.g. oral) and the intended form of the composition (e.g. beverage, yogurt, powder, capsules, and the like). The skilled person knows how to select a physiological or pharmaceutical carrier, which is suitable for the compositions as taught herein.

In an embodiment, the composition as taught herein may be in the form of a food composition, feed composition, feed supplement composition, food supplement composition or pharmaceutical composition. The composition is preferably suitable for consumption by a mammal, such as a human being, a pet or a production animal.

In an embodiment, the composition is a food or food supplement composition. The food or food supplement composition may be selected from the group consisting of a liquid, liquid beverage (including dairy beverage and fermented beverage), yogurt, cheese, gel, gelatine, gelatine capsule, powder, paste, pressed tablet, and gel cap. In a suitable embodiment, the composition is a liquid, preferably a liquid beverage (e.g. dairy beverage). The food or food supplement composition may be a dairy product, preferably a fermented dairy product, preferably a yogurt or a yogurt drink.

In an embodiment, the composition as taught herein may be a probiotic composition. Such probiotic composition may comprise any of the isolated intestinal bacterial strain as taught herein, or a strain derived therefrom.

In an embodiment, the composition as taught herein further comprises one or more additional beneficial isolated intestinal bacterial strain.

In an embodiment, the composition taught herein may be a symbiotic composition. It may be advantageous to add one or more prebiotic ingredients to the composition as taught herein, for example, to enhance the effects (e.g. production of butyric acid and/or butyrate or a derivative thereof) of the intestinal bacterial strain as taught herein.

In an embodiment, the one or more prebiotic ingredients may be any prebiotic ingredients, which are suitable to enhance the activity and/or stimulate the growth of the isolated intestinal bacterium, or a strain derived therefrom, as taught herein. Non-limiting examples of suitable prebiotic ingredients include fibers, cellobiose, maltose, mannose, salicine, trehalose, amygdalin, arabinose, melibiose, rhamnose and/or xylose.

In an embodiment, the composition as taught herein may comprise one or more ingredients which are suitable for promoting survival and/or viability of the bacterial strain or strain derived therefrom as taught herein during storage and/or during exposure to bile and/or during passage through the GI tract of a mammal (e.g. a human being). Non-limiting examples of such ingredients include an enteric coating, and controlled release agents allowing passage through the stomach. The skilled person knows how to select suitable ingredients for maintaining a bacterial strain viable and functional i.e. able to carry out their intended function(s).

In one embodiment, the compositions as taught herein may further comprise one or more ingredients, which further enhance the nutritional value and/or the therapeutic value the compositions as taught herein. For instance, it may be advantageous to add one or more ingredients (e.g. nutritional ingredients, veterinary or medicinal agents etc.) selected from proteins, amino acids, enzymes, mineral salts, vitamins (e.g. thiamine HCl, riboflavin, pyridoxine HCl, niacin, inositol, choline chloride, calcium pantothenate, biotin, folic acid, ascorbic acid, vitamin B12, p-aminobenzoic acid, vitamin A acetate, vitamin K, vitamin D, vitamin E, and the like), sugars and complex carbohydrates (e.g. water-soluble and water-insoluble monosaccharides, disaccharides, and polysaccharides), medicinal compounds (e.g. antibiotics), antioxidants, trace element ingredients (e.g. compounds of cobalt, copper, manganese, iron, zinc, tin, nickel, chromium, molybdenum, iodine, chlorine, silicon, vanadium, selenium, calcium, magnesium, sodium and potassium and the like). The skilled person is familiar with methods and ingredients that are suitable to enhance the nutritional and/or therapeutic/medicinal value of the compositions as taught herein.

The bacterial strain taught herein may be incorporated into the composition in lyophilized form, microencapsulated form (reviewed by, for example, Solanki et al. BioMed Res. Int. 2013, Article ID 620719), or any other form preserving the activity and/or viability of the bacterial strain.

The composition as taught herein may be a pharmaceutical composition. The pharmaceutical composition may be for use as a supplement. A pharmaceutical composition will usually comprise a pharmaceutical carrier, in addition to the bacterial strain taught herein. The carrier is preferably an inert carrier. The preferred form depends on the intended mode of administration and (therapeutic) application. A pharmaceutical carrier can be any compatible, nontoxic substance suitable to deliver bacteria of the bacterial strain taught herein to the GI tract of a subject. For example, sterile water, or inert solids may be used as a carrier, usually complemented with a pharmaceutically acceptable adjuvant, buffering agent, dispersing agent, and the like. A pharmaceutical composition as taught herein may be in liquid form, e.g. a stabilized suspension of bacteria of the bacterial strain taught herein, or in solid form, e.g., a powder of lyophilized bacteria of the bacterial strain taught herein. In case the bacterial strain taught herein is lyophilized, a cryoprotectant such as lactose, trehalose or glycogen can be employed. E.g., for oral administration, bacteria of the bacterial strain taught herein can be administered in solid dosage forms, such as capsules, tablets, and powders, comprising lyophilized bacteria, or in liquid dosage forms, such as elixirs, syrups, and suspensions. Bacteria of the bacterial strain taught herein, e.g., in lyophilized form, can be encapsulated in capsules such as gelatin capsules, together with inactive ingredients and powdered carriers, such as e.g. glucose, lactose, sucrose, mannitol, starch, cellulose or cellulose derivatives, magnesium stearate, stearic acid, sodium saccharin, talcum, magnesium carbonate and the like.

In an embodiment, the intestinal bacterium or strain derived therefrom as taught herein may be comprised in the composition as taught herein in an effective amount, e.g., ranging from about $10^4$ to about $10^{15}$ cells or colony forming units (CFU). For instance, the intestinal bacteria may be comprised in the composition in an amount of about $10^6$ or $10^7$ cells or CFU to about $10^{14}$ cells or CFU, preferably about $10^8$ cells or CFU to about $10^{13}$ cells or CFU, preferably about $10^9$ cells or CFU to about $10^{12}$ cells or CFU, more preferably about $10^{10}$ cells or CFU to about $10^{12}$ cells or CFU.

The compositions as taught herein may be produced by any conventional methods.

Methods and Uses of the Bacterial Strains and Compositions

In another aspect, the present invention is concerned with a bacterial strain as taught herein or a composition as taught herein for use as a medicament, for use as a food or food supplement, or for use as a probiotic and/or symbiotic.

The present invention further pertains to an isolated *Akkermansia glycaniphilus* strain as taught herein or the composition as taught herein for use in preventing and/or treating a disorder selected from the group consisting of metabolic syndrome, obesity, insulin-deficiency or insulin-resistance related disorders, type 2 diabetes, type 1 diabetes, inflammatory bowel disease (IBD), irritable bowel syndrome (IBS), glucose intolerance, abnormal lipid metabolism, atherosclerosis, hypertension, cardiac pathology, stroke, non-alcoholic fatty liver disease, alcoholic fatty liver disease, hyperglycemia, hepatic steatosis, dyslipidemias, dysfunction of the immune system associated with obesity (weight gain), allergy, asthma, autism, Parkinson's disease, multiple sclerosis, neurodegenerative diseases, depression, other diseases related to compromised barrier function, wound healing, behavioral disorders, alcohol dependence, cardiovascular diseases, high cholesterol, elevated triglycerides, atherosclerosis, sleep apnea, osteoarthritis, gallbladder disease, cancer, and conditions altering the physical integrity of the gut mucosal barrier such as food allergies, immaturity of the gut, e.g., due to a baby being born prematurely, exposure to radiation, chemotherapy and/or toxins, autoimmune disorders, malnutrition, and sepsis; and for use in promoting anti-inflammatory activity in the gut of a mammal.

The present invention also provides a method of modulating and/or promoting gut mucosal immune system function and/or maintaining and/or restoring and/or increasing the physical integrity of the gut mucosal barrier in a mammal, e.g., a human, said method comprising the step of administering the *Akkermansia glycaniphilus* strain as taught herein or the composition as taught herein to a mammal, e.g., a human, in need thereof.

In an embodiment, the bacterial strain as taught herein or the composition as taught herein is administered at least once a week, preferably at least twice a week, more preferably at least once a day, and even more preferably at least twice a day.

In an embodiment, the daily amount of *Akkermansia glycaniphilus* administered per day ranges from about $10^4$ to about $10^{15}$ cells or colony forming units (CFU). For instance, the intestinal bacteria may be administered in an amount of about $10^6$ or $10^7$ cells or CFU to about $10^{14}$ cells or CFU per day, preferably about $10^8$ cells or CFU to about $10^{13}$ cells or CFU per day, preferably about $10^9$ cells or CFU to about $10^{12}$ cells or CFU per day, more preferably about $10^{10}$ cells or CFU to about $10^{12}$ cells or CFU per day.

In an embodiment, the bacterial strain as taught herein or the composition as taught herein is administered to a subject that is overweight, or to a subject that is obese. In an embodiment, the subject is diagnosed with a metabolic disorder, e.g., an overweight and/or obesity related metabolic disorder. In another embodiment, said subject is at risk of developing a metabolic disorder, e.g., an overweight and/or obesity related metabolic disorder. For instance, said risk may be related to the fact that the subject is overweight or obese. Alternatively or additionally, said risk corresponds to a predisposition, e.g. a familial predisposition, to a metabolic disorder, e.g., an overweight and/or obesity related metabolic disorder.

The subject may be of any age group (e.g., infants, adults, elderly) and of any gender (male and female). In an embodiment, the mammal is an infant (e.g., new-born, baby, toddler or the like), particularly an infant which was born prematurely.

In an embodiment, the gut microbiota of a subject is depleted in *Akkermansia muciniphila* strain. For example, the proportion of *Akkermansia muciniphila* in the gut of the subjects may be less than 1%, preferably less than 0.5%, more preferably less than 0.1%, in number of *Akkermansia muciniphila* to the total number of bacterial cells in the gut.

The present invention also relates to the cosmetic use of *Akkermansia glycaniphilus* for promoting weight loss in a subject.

Therefore, the present invention also provides for a cosmetic composition comprising a cosmetically effective amount of *Akkermansia glycaniphilus*, and the use thereof for promoting weight loss in a subject. As used herein, a "cosmetically effective amount" refers of the amount of a cosmetic composition necessary and sufficient for promoting a cosmetic effect, such as, for example, for inducing weight loss in a subject.

In an embodiment, the cosmetically effective amount of *Akkermansia glycaniphilus* ranges from about $10^4$ to about $10^{15}$ cells or colony forming units (CFU). For instance, the intestinal bacteria may be administered in an amount of about $10^6$ or $10^7$ cells or CFU to about $10^{14}$ cells or CFU per day, preferably about $10^8$ cells or CFU to about $10^{13}$ cells or CFU per day, preferably about $10^9$ cells or CFU to about $10^{12}$ cells or CFU per day, more preferably about $10^{10}$ cells or CFU to about $10^{12}$ cells or CFU per day.

In an embodiment, the cosmetic composition as taught herein is administered at least once a week, preferably at least twice a week, more preferably at least once a day, and even more preferably at least twice a day.

The invention further provides a method for increasing the level of *Akkermansia glycaniphilus* in the gastrointestinal tract of a mammal, preferably a human, said method comprising the steps of:
administering the isolated *Akkermansia glycaniphilus* strain or the composition to said mammal; and
promoting the growth of said *Akkermansia glycaniphilus* strain in the GI tract of said mammal by administering a compound selected from the group consisting of compounds comprising glucosamine or derivatives of glucosamine such as N-acetyl-glucosamine as building blocks, and polyphenols, to said mammal.

A non-limiting example of a compound comprising glucosamine or derivatives or glucosamine is chitin. Polyphenols may, for example, be contained in cranberries, grapes or other plant-derived products as described (see Anhê F F et al. Gut Microbes. 2016 Feb. 22:0. [Epub ahead of print]).

The present invention is further illustrated, but not limited, by the following examples. From the above discussion and these examples, one skilled in the art can ascertain the essential characteristics of the present invention, and without departing from the teaching and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

EXAMPLES

Materials and Methods
Source of the Organism and Cultivation
During the isolation of mucolytic bacteria from fresh faeces obtained from the reticulated python (*Malayopython reticulatus*) housed in Burgers' Zoo (Arnhem, The Netherlands), strain Pyt$^T$ was recovered using an anaerobic basal medium that contained 0.5% mucin as the sole carbon and energy source as previously described as mucin medium (Derrien, Vaughan, Plugge & de Vos, 2004. Int J Syst Evol Microbiol 54:1469-1476). For comparison purposes *A. muciniphila* Muc$^T$ (CIP 107961$^1$) was used. Strain Pyt$^T$ was isolated using a dilution to extinction approach on mucin medium followed by a streaking on mucin plates consisting of mucin medium supplemented with 0.8% agar (Agar noble; Difco). Single colonies were picked, re-grown in mucin medium and re-streaked on mucin plates until purity was reached.

Genetic-Based Methods: Phylogenetic and Genomic Analysis

Nucleotide sequence analysis of a cloned 16S rRNA gene was performed to determine the phylogenetic affiliation of the strain Pyt$^1$. Total DNA was extracted using the Gram Positive DNA Purification Kit (Epicenter) and 16S rRNA gene sequences were amplified by PCR using the universal primers 27F and 1492R (Suzuki, Taylor & DeLong, 2000. Appl Environ Microbiol 66:4605-4614) and PCR products were purified using the High Pure PCR Cleanup Micro kit (Roche Diagnostics). To obtain an almost complete 16S rRNA gene sequence of strain $Pyt^1$, purified PCR products were cloned in *Escherichia coli* XL1-blue using the pGEM-T easy vector system (Promega) according to the manufacturer's instructions. Plasmid DNA was isolated from 44 transformant cultures using the QIAprep Spin Miniprep kit (Qiagen) and used as template for Sanger sequence analysis (performed by GATC) using insert-flanking T7 and SP6 promoter-targeted primers (Promega). Sequences were aligned using DNABaser and the alignment was corrected manually to ensure overlapping sequences. All cloned inserts were found to derive from an identical 16S rRNA gene and a sequence of 1439 bp was obtained. The 16S rRNA gene sequences of strain $Pyt^T$ and other members of the phylum Verrucomicrobia were aligned using the SINA aligner (http://www.arb-silva.de/aligner/) (Pruesse, Peplies & Glockner, 2012. Bioinformatics 28:1823-1829). Phylogenetic trees were reconstructed using ARB (Ludwig, Strunk, Westram et al., 2004. Nucleic Acids Res 32:1363-1371). Distances and clustering with both neighbour joining and maximum parsimony methods were determined by using bootstrap values based on 1000 replications.

A partial genome sequence of strain $Pyt^T$ was determined to further support the phylogenetic position and study its genomic relationships. The total DNA isolated as described above was used to prepare a MiSeq library that was subjected to next generation sequencing on an Illumina MiSeq Personal Sequencer with 250 bp paired-end reads and an insert size of 500 bp. Reads were assembled using Ray (k-mer 101) (Boisvert, Raymond, Godzaridis et al., 2012. Genome Biol 13:R122).

Annotation was carried out with an in-house pipeline consisting of Prodigal v2.5 for prediction of protein coding DNA sequences (CDS) (Hyatt, Chen, Locascio et al., 2010. BMC bioinformatics 11:119), InterProScan 5RC7 for protein annotation (Hunter, Jones, Mitchell et al., 2012. Nucleic Acids Res 40:D306-312), tRNAscan-SE v1.3.1 for prediction of tRNAs (Lowe & Eddy, 1997. Nucleic Acids Res 25:955-964) and RNAmmer v1.2 for prediction of rRNAs (Lagesen, Hallin, Rodland et al., 2007. Nucleic Acids Res 35:3100-3108). Additional protein function predictions were derived via BLAST identifications against the UniRef50 (Suzek, Huang, McGarvey et al., 2007. Bioinformatics 23:1282-1288) and Swissprot (UniProt-Consortium, 2014) databases (download August 2013). Subsequently, the annotation was further enhanced by adding EC numbers via PRIAM version 2013-03-06 (Claudel-Renard, Chevalet, Faraut et al., 2003. Nucleic Acids Res 31:6633-6639). Non-coding RNAs were identified using rfam_scan.pl v1.04, on release 11.0 of the RFAM database (Burge, Daub, Eberhardt et al., 2013. Nucleic Acids Res 41:D226-232).

For DNA-DNA hybridization (DDH) experiments, cells of strains $Pyt^T$ and $Muc^T$ were grown and harvested at stationary phase where after the pellet was resuspended in $H_2O$:iso-propanol (1:1). Hereafter, the Leibniz-lnstitut DSM-Z (Deutsche Sammlung fur Mikroorganismen und Zellkulturen, Braunschweig, Germany) performed DDH experiments as previously described (Cashion, Holder-Franklin, McCully et al., 1977. Anal Biochem 81:461-466; Deley, Cattoir & Reynaert. A, 1970. Eur J Biochem 12:133; Huss, Festl & Schleifer, 1983. Syst Appl Microbiol 4:184-192).

The percentage G+C content of the genomic DNA of strain $Pyt^T$ was determined by the Leibniz-lnstitut DSMZ as previously described (Cashion, Holder-Franklin, McCully & Franklin, 1977. Anal Biochem 81:461-466; Mesbah, Premachandran & Whitman, 1989. Int J Syst Bacteriol 39:159-167, Tamaoka & Komagata, 1984. FEMS Microbiol Lett 25:125-128).

Phenotypic Characterization: Morphology, Physiology, and Chemotaxonomy

Gram staining was performed as described (Plugge, Zoetendal & Stams, 2000. Int J Syst Evol Microbiol 50 Pt 3:1155-1162). Cell morphology, motility and spore formation was monitored by phase-contrast microscopy, with cells grown for 2 days at 37° C. on mucin-based medium. The presence of a capsule was determined by staining the cells grown in mucin medium with an Indian ink suspension.

For scanning electron microscopy analysis, cells were fixed in 2% glutaraldehyde in 0.1 M phosphate buffer (pH 7.4) for 2 h at room temperature, and post-fixed with 2% osmium tetroxide for 30-60 min. Hereafter cells were dehydrated in a graded alcohol series (50%, 70%, 96% and 100%), lastly treated with hexamethyldisilazane, and mounted into aluminium stub and coated with platinum. Cells were subsequently studied with a FEI Quanta 250 FEG-scanning electron microscope.

Growth experiments were performed in duplicate for each strain, using 30 ml-serum bottles. The gas phase was 1.5 atm of $N_2/CO_2$ (80:20, v/v). Unless otherwise indicated, the general conditions were pH 6.5, temperature 37° C. Growth was monitored by measuring optical density at 600 nm (OD600) with a spectrophotometer (Ultraspec 10, Biosciences). Short chain fatty acids were measured using a Thermo Electron spectrasystem HPLC equipped with an Agilent Metacarb 67H column.

The optimum pH and temperature were measured in duplicate on brain—heart infusion (BHI; Difco) supplemented with 0.5% w/v hog gastric mucin (Type III, Sigma), and 0.05% w/v cysteine. Temperatures tested were 10-55° C., at intervals of 5° C.; growth was determined at pH 3.5-9, at intervals of 0.5 pH units (adjusted with HCl or NaOH) at 37° C.

Cultures were incubated for at least 1 month.

Growth on D-mannose, D-glucose, L-fucose, D-fructose, D-galactose, N-acetylglucosamine, N-acetylgalactosamine, D-cellobiose were tested in duplicate at a concentration of 10 mM in a basal medium previously described (Derrien, Vaughan, Plugge & de Vos, 2004. Int J Syst Evol Microbiol 54:1469-1476), supplemented with tryptone 16 g $l^{-1}$, and threonine 4 g $l^{-1}$. Growth was determined on D-glucose, D-maltose, D-lactose, D-mannitol, D-saccharose, salicine, D-xylose, L-arabinose, glycerol, D-cellobiose, D-mannose, D-melezitose, D-raffinose, D-sorbitol, L-rhamnose, and D-trehalose using API® 20A (bioMérieux, France) according manufacturer's instructions with one alteration: a basal medium as previously described (Derrien, Vaughan, Plugge & de Vos, 2004. Int J Syst Evol Microbiol 54:1469-1476) supplemented with tryptone 16 g $l^{-1}$, and 4 g $l^{-1}$ threonine was used to inoculate the API® 20A. Hereafter, catalase activity was determined by reaction with 3% (w/v) solution of $H_2O_2$. Indole and urease formation as well as gelatin and esculin hydrolysis were determined with API® 20A (bio-Mérieux, France) strips as well.

Antibiotic resistance was determined using the Etest method for both ampicillin and vancomycin (bioMérieux, Marcy l'Étoile, France). The minimal inhibitory concentration (MIC) was determined after 48 hours of incubation. In more detail, strain $Pyt^T$ was grown in mucin media and after reaching stationary phase 100 ul was plated onto BHI plates supplemented with 0.5% (v/v) hog gastric mucin (Type III, Sigma), and 0.05% (w/v) of cysteine-HCL (Sigma-ALdrich). Plates were incubated for 24-48 hours under strictly anaerobic conditions. The level of resistance was determined using the European Committee on Antimicrobial Susceptibility Testing (EUCAST) breakpoint table for interpretation of MICs for Gram-negative anaerobes (Version 5.0, valid from 2015-01-01).

For chemotaxonomy characterization, strains $Pyt^T$ and $Muc^T$ were grown and harvested at stationary phase and subsequently freeze dried. The analysis of cellular fatty acids was performed by the Leibniz-Institut DSMZ as previously described (Kampfer & Kroppenstedt, 1996. Can J Microbiol 42:989-1005).

Results

Phylogeny and Genomic Characteristics

The 16S rRNA gene nucleotide sequence of strain $Pyt^T$ included a continuous stretch of 1437 bp. Sequence similarity calculations after a neighbour-joining analysis indicated that the closest relatives of strain $Pyt^T$ was *A. muciniphila* $Muc^T$ (94.4%). The 16S rRNA sequence similarity is well under the current cut-off for species of 97% (Tindall, Rossello-Mora, Busse et al., 2010. Int J Syst Evol Microbiol 60:249-266). Remarkably, the 16S rRNA gene sequence of strain $Pyt^T$ showed 99.7% similarity to an uncultured clone derived from faeces from a Dugong, a marine mammal (AB264081). Lower sequence similarities (<90.0%) were found with representatives of all validly described genera that belong to the phylum of the Verrucomicrobiae, including the Rubritaleaceae, Akkermansiceae, and Verrucomicrobiacea families.

Strain $Pyt^T$ showed relatively low DDH similarity to the type strain $Muc^T$ (28.3%±5.2). The GC content was determined to be 58.2 mol %.

The complete genome of strain $Pyt^T$ was determined by single molecule PacBio sequencing and found to be composed of single chromosome that is 3,074,121 bp long, with a GC content of 57.6%. The PytT genome is 400 kb larger than the genome of strain $Muc^T$ (2.66 Mbp). The calculated DNA G+C content % of strain $Pyt^T$ 57.6% is in good agreement with the experimentally determined value (58.2%) but somewhat higher than that of strain $Muc^T$ (56.0%). The Blast similarity (>5 kb) of the genome of strain $Pyt^T$ compared to that of strain $Muc^T$ was 82.0%. The average nucleotide identity (ANI) of the genome of strain $Pyt^T$ compared to the genome of strain $Muc^T$ was 79.7%. It has been suggested that ANI can accurately replace DDH (Goris, Konstantinidis, Klappenbach et al., 2007. Int J Syst Evol Microbiol 57:81-91). The present data confirm this for the phylum of Verrucomicobia and show that both the ANI and the DDH similarity are well under the current species cut-off of 70% DDH and 95% ANI.

The genome of strain $Pyt^T$ reflects its mucin-degrading capacity as it is predicted to encode for 55 glycoside hydrolases, 28 of which are predicted to be secreted, 5 fucosidases, 3 of which are predicted to be secreted, and 7 sialidases, 6 of which are predicted to be secreted. To degrade the mucin glycoprotein it needs to cleave the sulfate groups that can be attached at the end of to the glycan chains. Strain $Pyt^T$ is predicted to code for 14 sulfatases, 9 of which are predicted to be secreted. The PytT genome also contains genes for cytochrome bd ubiquinol oxidase and a Ni-dependent hydrogenase pointing towards the potential for aerobic respiration that it might use in the oxic-anoxic interface of the intestinal mucin layer.

The mucin glycans consist of mainly galactose, N-acetylglucosamine, N-acetylgalactoseamine, and strain $Pyt^T$ is able to use these all as growth substrate. In contrast with strain *A. muciniphila* $Muc^T$, strain $Pyt^T$ is able to use galactose as sole carbon source, while producing mainly propionate, acetate and small amounts of succinate. Growth on galactose is relatively slow (>1 week) compared to the growth on mucin (<16 hours). Genome predictions indicated that strain $Pyt^T$ only encodes the canonical Leloir pathway enzymes galactokinase (GalK) and UDP-glucose 4-epimerase (GalE). These are also predicted to be encoded by strain $Muc^T$ (van Passel, Kant, Zoetendal, Plugge, Derrien, Malfatti, Chain, Woyke, Palva, de Vos & Smidt, 2011. Plos one 6:e16876). However, in the genome of strain $Pyt^T$ but not in that of strain $Muc^T$, we could identify 8 genes predicted to code for proteins with a galactose-binding domain, 7 of which are secreted. It is likely that a yet unknown galactose-metabolizing pathway operates in strain $Pyt^T$ and these genes may be involved in a system to bind and transport galactose.

Morphology

Cells are oval-shaped, non-motile and stain Gram-negatively. The long axis of single cells is 0.6-1.0 μm when grown in a mucin-based medium. Cells occur singly, in pairs, in short chains and in aggregates. On mucin-based agar grown for 48 hours at 37° C., strain $Pyt^T$ showed small white colonies with 0.7 mm diameter. SEM revealed the existence of filamentous structures connecting individual bacterial cells. Cells of strain $Pyt^T$ could exclude indian ink, characteristic of capsule-possessing bacteria.

Physiology

Strain $Pyt^T$ was a strict anaerobe, growing with L-cysteine, and/or sulfide as reducing agents. Growth occurred at 15-40° C. and pH 5.0-7.5, with optimum growth at 25-30° C. and pH 6.0. Compared to strain $Muc^T$, strain $Pyt^T$ grows at slightly lower temperatures and pH (Table 1). Its optimal temperature of 30° C. fits with the habitat of strain $Pyt^T$ as the python is ectothermic and depends on external heat sources to regulate its body temperature and is therefore lower than that of human or small mammals that serve as its prey (Wang, Zaar, Arvedsen et al., 2002. Comp Biochem Physiol A Mol ltegr Physiol 133:519-527). In the *Python bivittatus*, a relative of the *Malayopython reticulatus*, the gastrointestinal pH varied from 6.5 (stomach) to 7.6 (cecum) while fasting, and from pH 2-3 (stomach), 7-8 (esophagus, distal small intestine, cecum, and proximal large intestine), to 5-6.7 (distal esophagus, proximal stomach, and distal large intestine) after feeding (Secor, Boback & Lignot, 2006. lntegr Comp Biol 46). This indicates that the optimal pH of strain $Pyt^T$ (pH of approximately 6.0) might correspond to colonization of the distal large intestine.

Growing best in mucin medium, and capable of using mucin as carbon, energy and nitrogen source, strain $Pyt^T$ formed acetate, propionate and 1,2-propanediol. Strain $Pyt^T$ could grow without vitamins on mucin medium but was also able to grow slowly on brain-heart infusion medium and in a basal medium on N-acetylglucosamine, N-acetylgalactosamine, D-glucose, D-lactose and D-galactose in the presence of tryptone 16 g $l^{-1}$, and 4 g threonine. There was no growth on D-mannose, L-fucose, D-cellobiose or D-fructose in basal medium supplemented with tryptone 16 g $l^{-1}$, and threonine 4 g $l^{-1}$.

Using API® 20A (bioMérieux, France) strips with basal medium supplemented with tryptone 16 g $l^{-1}$, and 4 g threonine, growth of strain $Pyt^T$ was observed for D-glucose, D-maltose, and weak growth on D-lactose, while no growth was observed for D-mannitol, D-saccharose, salicine, D-xylose, L-arabinose, glycerol, D-cellobiose, D-mannose, D-melezitose, D-raffinose, D-sorbitol, L-rhamnose, D-trehalose. Catalase activity was positive. Indole and urease formation were negative, gelatin and esculin hydrolysis positive.

Strain Pyt$^T$ is able to use lactose as sole carbon source while producing mainly propionate and acetate. Growth on lactose is slower (Td approximately 4 hours) than the growth on mucin (Td approximately 1 hour). Quantification of fermentation products by HPLC analysis revealed initial cleavage of lactose into glucose and galactose. Hereafter, both glucose and galactose were converted into mainly propionate and acetate and small amounts of succinate. The reticulated python is not a lactating mammal, so therefore it is unexpected that strain Pyt$^T$ can use lactose as growth substrate. However, in the mucin glycoprotein there are numerous β4 glycolytic linkages (Linden, Sutton, Karlsson et al., 2008. Mucosal Immunol 1:183-197). Lactose has a similar β4 linkage that links glucose to galactose. Hence, to use mucin as growth substrate strain Pyt$^T$ needs to be able to degrade this glycan linkage and hence it is feasible that strain Pyt$^T$ can degrade lactose using the same enzyme as it normally uses for the degradation of mucin.

Analysis using the Etest method (bioMérieux, France) showed strain Pyt$^T$ to be relatively resistant to ampicillin (Minimal Inhibitory Concentration—MIC—value of 32 ug/ml) and vancomycin (MIC value of 24 ug/ml) but sensitive to all other clinically relevant antibiotics including cephalosporins, fluorquinolones, aminoglycosides, macrolides, tetracyclines, metronidazole, chloramphenicol, rifampicin or cholistin.

The results of the physiological characterization of strain Pyt$^T$ are in the species description and indicated in Table 1 in comparison with other members of the Verrucomicrobiae.

Colonies appear white with a diameter of 07 mm in soft agar mucin medium. Cells of strain Pyt$^T$ exclude Indian ink, characteristic of capsule-possessing bacteria. Growth occurs at 15-40° C. and pH 5.0-7.5, with optimum growth at 25-30° C. and pH 6.0. Strictly anaerobic or microaerophilic. Able to grow on gastric mucin and brain—heart infusion, and in a basal medium supplemented with tryptone 16 g l$^{-1}$, and 4 g threonine on N-acetylglucosamine, N-acetylgalactosamine, glucose, lactose and galactose. There was no growth on L-fucose, D-cellobiose or D-fructose in basal medium supplemented with tryptone 16 g l$^{-1}$, and 4 g threonine. Using API® 20A (bioMérieux, France) with the same basal medium supplemented with tryptone 16 g l$^{-1}$, and 4 g l$^{-1}$ threonine, growth was observed for D-glucose, D-maltose, and weak growth on D-lactose, while no growth was observed for D-mannitol, D-saccharose, salicine, D-xylose, L-arabinose, glycerol, D-cellobiose, D-mannose, D-melezitose, D-raffinose, D-sorbitol, L-rhamnose, D-trehalose. Catalase activity was positive. Indole and urease formation were negative, gelatin and esculin hydrolysis were positive. Capable of using mucin as sole carbon, energy and nitrogen source. Growth occurs without vitamins. DNA G+C content is 58.2 mol %. Main cellular fatty acids are anteiso-$C_{15:0}$, $C_{15:0}$ and $C_{16:0}$. Isolated from reticulated python faeces in Wageningen, The Netherlands. Type strain is Pyt$^T$ (=DSM 100705=CIP 110913T).

The invention claimed is:

1. A composition comprising an isolated *Akkermansia glycaniphilus* strain and a physiologically acceptable carrier,

TABLE 1

Physiological characteristics of the type strains of the Akkermansia species in comparison with representatives of other genera of the family Verrucomicrobiae (subdivision I). Data taken from (Hedlund, 2010. Phylum XXIII. Verrucomicrobia phyl. nov. In Bergey's Manual of Systematic Bacteriology. 2$^{nd}$ edition: Springer-Verlag, New York). Strains: 1, *A. glycanophilus* Pyt$^T$; 2, *A. muciniphila* Muc$^T$; 3, *Rubritalea* (based on *R. marina, R. sabuli, R. spongiae, R. squalenifaciens,* and *R. tangerina*); 4, *Prosthecobacter* (based on *P. debontii, P. dejongeii, P. fusiformis* and *P. vanneervenii*); 5, *Verrucomicrobium* (based on *Verrucomicrobium spinosum*); +, Positive; -, negative; (+), weakly positive; †, in the pressence of tryptone 16 g l$^{-1}$ and 4 g l$^{-1}$ threonine; ‡, depends on species. All strains are negative for motility, and negative for a requirement for vitamins. All strains are sensitive to ampicillin.

| Characteristic | 1 | 2 | 3 | 4 | 5 |
|---|---|---|---|---|---|
| Cell morphology | Oval-shaped | Oval-shaped | Coccoid or rod shaped | Fusiform rod-shaped | Fusiform rod-shaped |
| Cell size (μm) | 0.6-1.0 | 0.6-1.0 | 0.5-1.0 or 0.5-1.0 × 0.8-1.5 | 0.5 × 2.0-8.0 | 0.8-1.0 × 1.0-3.8 |
| Aerobic growth | − | − | + | + | + |
| Temperature range for growth (° C.) | 15-37 | 20-40 | 4-37‡ | 1-40‡ | 26-34 |
| Optimal temperature (° C.) | 30 | 37 | 30-37‡ | nd | 26-33 |
| pH range for growth | 5.0-7.5 | 5.5-8.0 | 6.5-8.5‡ | nd | nd |
| Optimal pH for growth | 6.0 | 6.5 | nd | nd | nd |
| Capsule | + | + | nd | nd | nd |
| Growth on: | | | | | |
| Glucose | +† | +† | + | + | + |
| Galactose | +† | − | +/−‡ | + | + |
| Fucose | − | + | | | |
| Fructose | − | − | + | +/−‡ | + |
| Cellobiose | − | − | +/−‡ | + | + |
| N-Acetylglucosamine | +† | +† | +/−‡ | +/−‡ | + |
| N-Acetylgalactosamine | +† | +† | +/−‡ | nd | nd |
| Mucin | + | + | nd | nd | nd |
| DNA G + C content (mol %) | 58.2 | 47.6 | 47.7-52.4 | 54.6-60.1 | 57.9-59.3 |

Description of *Akkermansia glycanophilus* sp. nov.

*Akkermansia glycanophilus* (gly.ca.ni'phi.la. L. neut. n. glycan derived from glycan; L. n. philos friendly to; N.L. m. adj. glucanophilus glycan-loving).

Cells are oval-shaped, non-motile and stain Gram-negatively. The long axis of single cells is 0.6-1.0 μm in a mucin-based medium. Cells occur singly, in pairs, in short chains and in aggregates. Cells are covered with filaments.

wherein said *Akkermansia glycaniphilus* is present in lyophilized or microencapsulated form.

2. The composition according to claim 1, wherein said *Akkermansia glycaniphilus* is capable of growing on mucin as sole carbon and nitrogen source.

3. The composition according to claim 1, wherein said *Akkermansia glycaniphilus* is capable of growing on mucin as sole carbon and nitrogen source and capable of growing on N-acetylglucosamine, N-acetylgalactosamine, glucose, lactose, maltose or galactose as sole carbon source.

4. The composition according to claim 1, wherein said *Akkermansia glycaniphilus* strain is the strain deposited as CBS141023, or a functionally equivalent strain that has been derived therefrom.

5. The composition according to claim 1, which is a pharmaceutical composition.

6. The composition according to claim 1, wherein said *Akkermansia glycaniphilus* is present in an amount ranging from about $10^4$ to about $10^{15}$ cells.

7. The composition according to claim 1, which is a probiotic and/or a symbiotic.

* * * * *